United States Patent [19]
Mosquet et al.

[11] Patent Number: 5,629,452
[45] Date of Patent: May 13, 1997

[54] PROCESS FOR THE PREPARATION OF POLYOXYALKYLATED AMINES

[75] Inventors: Martin Mosquet, Pithiviers; Jean-Pierre Guicquero, Santeny; Pierre Le Perchec, Lyons; Yves Chevalier, Irigny, all of France

[73] Assignee: Chryso, Chilly-Mazarin, France

[21] Appl. No.: 307,710

[22] PCT Filed: Apr. 9, 1993

[86] PCT No.: PCT/FR93/00364

§ 371 Date: Dec. 5, 1994

§ 102(e) Date: Dec. 5, 1994

[87] PCT Pub. No.: WO93/21254

PCT Pub. Date: Oct. 28, 1993

[30] Foreign Application Priority Data

Apr. 10, 1992 [FR] France .................. 92 04673

[51] Int. Cl.⁶ .................................. C07C 211/03
[52] U.S. Cl. .......................... 564/505; 564/504
[58] Field of Search ........................ 564/475, 477, 564/462, 505, 504, 506, 507

[56] References Cited

U.S. PATENT DOCUMENTS

| 2,871,266 | 1/1959 | Riley ........................ 260/584 |
| 3,118,000 | 1/1964 | Dupré et al. ................ 564/475 |
| 4,605,773 | 8/1986 | Maloney et al. ............. 564/505 |

FOREIGN PATENT DOCUMENTS

| 849343 | 6/1976 | Belgium. |
| 0268920 | 11/1987 | European Pat. Off.. |
| 0373860 | 12/1989 | European Pat. Off.. |

OTHER PUBLICATIONS

N.V. Ptitsyna et al., "Synthesis of Polyethylene Glycols of Molecular Weight Above 10,000 by Anionic Polymerization," 300 Polymer Science U.S.S.R., vol. 22 (1980) No. 11, Oxford, Great Britain.

Nakanishi, "Low–Molecular–Weight Vinyl Chloride Polymers"; Chem Abs. 87:13622y (1977).

Arisawa et al., "Suspension–Polymerizing Vinyl Chloride"; Chem Abs., 87:136823z (1977).

Hata et al., "Vinyl Acetate Copolymer"; Chem. Abs., 87:136824a (1977).

Rada et al., "Recycling of Volatile Organic Components in Polycondensation Reactions"; Chem Abs., 87:136819c (1977).

Akimoto, "Pentaerythritol Polyether"; Chem. Abs., 87:136821x (1977).

Stresinka et al., "Articles from Integral Polyurethane Foams"; Chemical Abstracts, 87:136820w (1977).

Yinglin et al., "A Convenient Preparation of Diamino Oligoethylene Glycols and Amino Polyethylene Glycols", Synthetic Communcations, 21(1), 79–84 (1991).

Zalipsky et al., "Attachment of Drugs to Polyethylene Glycols" Eur. Polym. J. vol. 19, No. 12, pp. 1177–1183, 1983.

Weidenbächer et al., "Oxietilarea Unor Amine Alifatice Primare Si Secundare" Revista de Chimie, 36, Nr. 1, 1985.

Broze et al., "Some New Easy Routes for the Specific Functionalization of Polymers by Pendant or End Amino Groups" Makromol. Chem. 178, 3171–3174 (1977).

Sépulchre, "Specific Functionalization of Polyoxirane by Amino, Carboxyl, Sulfo, and Halogeno End Groups" Makromol. Chem. 184, 1849–1859 (1983).

Primary Examiner—Brian M. Burn
Attorney, Agent, or Firm—Cummings & Lockwood

[57] ABSTRACT

A process for the preparation of polyoxyalkylated compounds comprising at least one primary or secondary amine function is provided comprising reacting at least one aminoalcoholate (B) produced from an amino-alcohol (A) including at least one OH group and at least one primary or secondary amine function, by replacing a fraction or all the OH groups by OM groups, M being selected from sodium, potassium, rubidium and cesium, with an oxirane, a mixture of oxiranes or a sequence of oxiranes, in an aprotic and anhydrous solvent, in an anhydrous atmosphere and at a temperature of between about 0° C. and 200° C.

29 Claims, No Drawings

PROCESS FOR THE PREPARATION OF POLYOXYALKYLATED AMINES

This application is a 371 of PCT/FR93/00364, filed Apr. 9, 1993.

The present invention concerns a preparation process for compounds containing at least one primary or secondary amine function and at least one polyoxyalkylated chain.

For the synthesis of such compounds, several pathways have been proposed in the prior art.

The first of these pathways consists of treating a polyoxyalkylated molecule having a terminal group that can be transformed into an amine function.

Thus the preparation of polyoxyethylated amines from polyethylene glycol is known. The study "Eur. Polym. J. Vol. 19, No. 12, pp. 1177–1183, 1983" of Zalipsky describes the preparation of amino-polyethylene glycol from polyethylene glycol by modifying the terminal hydroxyl function by a chlorine atom, then replacing this chlorine atom by an azide function, which is reduced in the presence of a catalysts.

Other more recent processes such as that of Yinglin, in "Synthetic Communications 21, (1), 79–84 (1991)" effect the preparation of amino-polyethylene glycol from polyethylene glycol. According to these processes, a tosyl radical is fixed onto the terminal hydroxyl function and then the product obtained is reacted with potassium phthalimide or sodium diformamide to arrive at the desired aminated compound.

Belgian patent No. 849,343 describes the preparation of polyoxyethylenes of secondary amines conforming to the following formula (I):

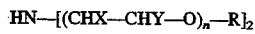

in which:

R is an alkyl radical, saturated or unsaturated, having 9 to 24 carbon atoms, a cyclohexyl radical or an aryl radical possibly bearing alkyl groups, X and Y each represent a hydrogen atom or a methyl radical, but cannot both designate a methyl radical, and, n is a whole number from 1 to 15, or, when R is a phenyl or tosyl radical, a whole number from 2 to 15.

To prepare these compounds, ox[y]alkylates conforming to the following formula (II) are reacted:

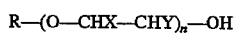

in which R, X, Y and n have the definitions given above, in liquid phase, with ammonia and hydrogen in the presence of hydrogenation-dehydrogenation catalysts, at a temperature of 150° C. to 250° C. and under an absolute pressure of 0.5 to 1.5 atmosphere.

Such processes, while they are economically acceptable, present, however, the principal disadvantage of requiring several steps, because amination can only be realized in last place, when the polyoxyethylate part has reached the desired length.

A second synthesis pathway for polyoxyalkylated amines consists of preparing compounds according to formula (I) by adding propylene or ethylene oxide onto molecules already having an amine function.

This generally leads to additions of oxide onto the nitrogen atom of the amine function, which then loses its primary or secondary nature.

In order to prevent polyoxyalkylation on the nitrogen atom of the amine function, it has been proposed to begin with secondary or primary amines protected by steric hindrance by means of a branched group.

Thus U.S. Pat. No. 2,871,266 describes a preparation process for secondary mono(polyoxyalkylated) amines from encumbered amines in the form of tert-carbinamine of the formula:

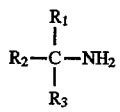

in which R1, R2 and R3 are alkyl radicals whose total number of carbon atoms varies from 7 to 23.

In order to form the secondary mono(polyoxyalkylated) amine, it is necessary to first form an N-hydroxyethylated derivative from this tert-carbinamine and then to react this intermediate product with ethylene or propylene oxide in the presence of an alkaline catalyst.

Such a process therefore has the disadvantage of requiring the presence of a carbon encumbered at alpha of the nitrogen by groups having at least 7 carbon atoms and only permits obtaining secondary polyoxyalkylated amines whose hydrogen is poorly reactive.

A third synthesis pathway of polyoxyalkylated amines consists of starting with an amino-alcohol whose amine function is protected and transforming it into an inert function with epoxides, and then effecting the addition of propylene or ethylene oxide.

This third pathway is notably described in "Makromol. Chem. 184, 1849–1859, 1983" in the case of preparation of polyoxiranes having primary terminal amine functions from amino-alcohol.

The amine function of the initial amino-alcohol is first protected by means of a succinyl group. Then a potassium alcoholate is formed by means of potassium dihydronaphthylide. The alcoholate can then open the ethylene oxide and the desired primary polyoxyethylated amine is obtained after a polyaddition of ethylene oxide followed by a neutralization, a regeneration of the amine function, and then an elimination of secondary products formed by the regeneration.

There does not exist in the prior art a process permitting preparing compounds having at least one primary or secondary amine function and at least one polyoxyalkylated chain, which does not include the protection step of amine functions.

The applicant, in collaboration with the CNRS and GIE LAFARGE COPPEE RECHERCHE, has developed a simple process for preparation of compounds furnished with at least one primary or secondary amine function and at least one polyoxyalkylated chain. Surprisingly, this process does not include any amine function protection step.

The process of the present invention is characterized in that one reacts:

at least one amino-alcoholate (B) obtained from an amino-alcohol (A) containing at least one OH group and at least one primary or secondary amine function, by replacing a fraction or all of the OH groups by OM groups, M being chosen from among sodium, potassium, rubidium and cesium, said amino-alcohol (A) and amino-alcoholate (B) being free of groups able to react together or with a function carried by the amino-alcohol (A) or amino-alcoholate (B) under the reaction conditions of the process, such as an acid or halogen group;

with an oxirane, a mixture of oxiranes or a sequence of oxiranes, in an aprotic and anhydrous solvent, under an anhydrous atmosphere and at a temperature comprised between 0° C. and 200° C., so as to fix onto each atom of oxygen originating either from an OH group or an OM group a series of similar or different "m" units, m being a whole number greater than or equal to 1, preferably comprised between 1 and 10,000, in particular comprised between 1 and 500 and especially comprised between 1 and 250, said "m" units conforming to the following formula:

$$-[C(R_1)(R_2)-C(R_3)(R_4)-O]-$$

in which $R_1$, $R_2$, $R_3$ and $R_4$ are similar or different and can be chosen from the group made up of:
the hydrogen atom
monovalent radicals, saturated or not, alkyl, cyclo-alkyl or aryl,
said radicals possibly containing various nonreactive substituents with regard to an amine function and an alcoholate function, such as ether or tertiary amine functions.

The process according to the invention is possibly followed by a second step during which the product obtained previously in a manner known in and of itself can be neutralized or functionalized, by fixing onto each terminal oxygen atom a polyoxyalkylated chain, for example, a hydrogen atom, a possibly substituted radical, saturated or not, alkyl or cycloalkyl, or an aryl radical.

The process according to the invention can also be followed by other additions of one or several oxiranes of different chemical nature, preferably under the conditions recommended in the invention. In such a way, polyoxyalkylated chains are prepared having oxirane sequences different from one sequence to another.

By potassium, rubidium, cesium or sodium alcoholate function is understood in the present invention, respectively, the OK, ORb, OCs or ONa groups carried by a carbon atom.

The process according to the present invention has the advantage of being selective while being simple, of being able to be implemented under easy operating conditions, with the initial products currently employed in organic synthesis, and even of being ready for an industrial application with respect to both economy and safety.

Moreover, it permits control of the degree of polyoxyalkylation, which offers the advantage of being able to vary the hydrophilic or hydrophobic character of the molecule. In fact, due to the fact that the introduction of oxirane can be realized progressively in the reaction medium, it is sufficient to interrupt it as soon as the desired average polyoxyalkylated chain length is attained.

The process of the invention is based on the surprising discovery that it is possible to obtain in a highly selective manner the opening of oxiranes by alcoholate functions alone, without previous protection of the primary or secondary amine functions of the initial product, or recourse to a catalyst.

This result is obtained according to the invention when the alcoholate functions are sodium, potassium, rubidium or cesium alcoholate functions. It has been found that the polyaddition is effected selectively on oxygen atoms originating from an OH group or an OM group, with the condition that the counter-ion M is a sodium, potassium, rubidium or cesium cation. The majority of primary and/or secondary amine functions, even if unprotected, can therefore be conserved.

On the other hand, if the reaction is effected from an amino-alcohol (A), in other words, when the initial product does not contain the OM group, selectivity of the reaction is lost, and consequently, polyaddition can be produced on the primary or secondary amine function or functions of the initial product.

By means of the following tests given by way of illustration and non-limiting, we will present the advantages of the invention.

An amino-alcoholate (B) is prepared from an amino-alcohol (A) that has been subjected to the action of a base (by transformation of OH groups into OM groups), and a polyoxyalkylation is realized with ethylene oxide in tetrahydrofuran.

The amino-alcoholates were prepared by means of different bases with the objective of comparing the influence of the nature of the M cation bound to the amino-alcoholate. The operating conditions, other than those presented in the following table, are the same for these four tests:

| No. | Amino-alcoholate (B) | C1 | C2 | B⁻ | F (%) |
|---|---|---|---|---|---|
| 1 | ⁻OCH₂CH₂NH₂ | 215.17 | 2.15 | DPMK⁺ | <3% |
| 2 | ⁻OCH₂CH₂NHCH₃ | 215.0 | 2.15 | DPMK⁺ | <31% |
| 3 | ⁻OCH₂CH₂—NHCH₃ | 210.0 | 2.10 | DPMNa⁺ | 45[a] |
| 4 | ⁻OCH₂CH₂—NHCH₃ | 207.0 | 2.07 | NaNH₂ | 55[a] |

Notes:
C1: concentration of amino-alcoholate (B) in the medium (expressed in $10^{-3}$ mole per liter),
C2: concentration of ethylene oxide in the medium (expressed in moles per liter),
B⁻: base used to generate the alcoholate function from the alcohol function,
DPMK⁺: diphenylmethylpotassium
DPMNa⁺: diphenylmethylsodium
F: amino-alcoholate (B) molar fraction whose amine function has lost its initial primary or secondary character,
[a]The polyadditions are rather slow in these cases. The values of F are then measured for partial consumption of oxirane of 45% and 50%, respectively, for the polyadditions of tests 3 and 4. These high values of F result from the addition of oxirane onto the nitrogen of the amine function.

A large difference in selectivity appears, depending on whether the cation used is the sodium cation or the potassium cation. In fact, a total selectivity is observed when the alcoholate function reacting with oxirane, in the case of ethylene oxide, is a potassium alcoholate function.

In a general way, it is preferable to implement the process according to the invention by beginning with an amino-alcoholate (B) whose cations bound to the alcoholate functions are potassium, rubidium or cesium cations. It is more particularly advantageous to begin with an amino-alcoholate (B) whose cations are potassium cations.

Amino-alcohols (A) that can serve as initial products for the preparation of amino-alcoholate (B) advantageously conform to the following formula (III):

$$[(HNRi)_j Q](OH)_{(r+q)}$$

in which:
j is the number of primary or secondary amine functions, which are identical or different from one another, j varying from 1 to 10 inclusive,
r is the sum of the number of OH groups carried by all the Ri groups, and q is the number of OH groups carried by Q, r+q being greater than or equal to 1 and may reach 10,
Q represents an organic radical comprising 2 to 50 carbon atoms,
each Ri is a hydrogen atom or an organic radical comprising 1 to 50 carbon atoms,
when the amino-alcohol (A) contains more than one primary or secondary amine function, the Ri groups may be similar to or different from one another,
Q and Ri may be heteroatom carriers and/or may have different substituents, such as ether or tertiary amine functions, Q, N and Ri groups together can form one or several rings, this ring or rings being able, moreover, to contain one or several other heteroatoms, Q and Ri must be free of groups able to react together or with other groups carried by the amino-alcohol (A) or the amino-alcoholate (B) under the reaction conditions of the process according to the invention.

Among the amino-alcohols (A), by way of example, the following currently used compounds can be cited:

ethanolamine diethanolamine the propanolamines

N-methylethanolamine 4-amino-cyclohexanol diamino-2-propanol

N-decylethanolamine

The amino-alcoholate (B) necessary for the implementation of the process according to the invention can be prepared according to any known preparation method for a sodium, potassium, cesium or rubidium alcoholate. Preferably, the amino-alcoholate (B) is prepared by contacting an amino-alcohol (A) having at least one OH group and at least one primary or secondary amine function with a base carrying the desired cation or cations.

The base used is preferably diphenylmethylpotassium, potassium hydride, potassium amide or finely divided potassium. In fact, such bases have the advantage of quantitatively transforming the alcohol functions into alcoholate functions at moderate temperature, for example 30° C.

The use of such bases permits, moreover, preparing amino-alcoholates (B) in the solvent where the process according to the invention will be conducted. Bases such as sodium, potassium, rubidium or cesium hydroxide or light alcoholates of sodium, potassium, rubidium or cesium could also be used. But in this case, the formation reaction of the OM alcoholate function presents several disadvantages:

this reaction is equilibrated, this reaction leads to the formation of water or light alcohol which must be eliminated from the reaction mixture, for example, by evaporation, before undertaking the polyoxyalkylation reaction, because if it is not, a part of the oxiranes will be consumed by this water or these light alcohols.

According to the process of the invention, it is not necessary that all of the OH groups of the initial product be transformed into OM groups. Polyoxyalkylation is effected on all of the oxygen atoms, whether they have an OH group or an OM group.

It is recommended, however, in order to obtain a satisfactory selectivity, that the number of OM groups be greater than 30%, preferably greater than 40% of the sum of the number of OM groups and the number of OH groups. These percentages are particularly advantageous and procure a high selectivity when M is the potassium cation. Nevertheless, they can vary according to the operating conditions and the type of M cation being used. In addition, the addition to the solvent of compounds with complexing properties, such as cryptates, can drive these percentages towards the low end.

In other words, to implement the process according to the invention and arrive at a final product with polyoxyalkylated chains essentially bound to oxygen atoms and not to nitrogen atoms originating from an amine function, it is recommended to begin with the product of the reaction of amino-alcohol (A) with a base quantity such that the ratio of the number of M cations carried by the base to the number of OH groups of the amino-alcohol (A) is greater than 0.3 and preferably greater than 0.4. When this ratio is less than 1, the product obtained is a mixture of amino-alcoholates (B) differing by the number of OH groups replaced by OM groups. This mixture can even still contain amino-alcohol (A). This is the case notably when the initial amino-alcohol (A) has only a single OH group.

Among the oxiranes suitable for the invention can be cited ethylene oxide, propylene oxide, butylene oxide, amylene oxide, octylene oxide, styrene oxide, methylstyrene oxide, cyclohexane oxide, as well as their various substituted derivatives. It is also possible to use a mixture of these oxiranes or several different oxiranes successively, so as to alternate polyoxyalkylated chains of different chemical nature.

Preferably, the oxirane used is chosen from the group made up of ethylene oxide, propylene oxide, styrene oxide and their mixtures. More preferably still, ethylene oxide is chosen.

The quantity of oxirane to be added is only a function of the chain length desired and the number of OH or OM groups. It is independent of the quantity of base that is used to prepare the initial product.

According to the invention, the process is conducted in an aprotic and anhydrous solvent, in order not to regenerate the alcohol functions.

By aprotic solvent is understood here a solvent free of acid hydrogen under the operating conditions.

The solvent is chosen preferably from among highly polar solvents in order to facilitate the dissociation of sodium, potassium, rubidium or cesium cations of the alcoholate functions. The solvents particularly well suited to the process according to the invention are tetrahydrofuran, diglyme (diethylene glycol dimethyl ether), dimethyl sulfoxide or hexamethyl phosphoramide.

The reaction of oxirane addition onto the oxygen atoms is conducted in a manner known in and of itself, like any reaction of addition of an oxirane onto an alcoholate.

The polyaddition reaction must be effected under anhydrous atmosphere in order to prevent the introduction of water into the reaction medium, which regenerates the alcohol functions and therefore disturbs the polyaddition. For this, one can work under nitrogen, argon or under any other gas inert with regard to the reaction medium.

The reaction temperature of this first step is generally comprised between 0° C. and 200° C. according to the solvent used and preferably between 20° C. and 120° C.

The durations and the reaction pressures are known to the expert and are a function of the operating mode followed.

The product derived from the process according to the invention can react with all compounds able to react with an alcoholate. It can be subjected to a treatment to regenerate the alcohol function or to modify its functionality.

One can advantageously profit from its basicity to introduce a new functionality. Thus, for example, the reaction medium can be acidified to fix a proton or add an alkylation agent such as dimethyl sulfate or methyl iodide to realize an alkylation. The agent employed to effect this functionalization will, however, be chosen by taking into account the presence of amine functions, in order to not affect them.

By means of the process according to the invention, the yields are high and the final products are of a purity suitable for the majority of their applications.

The process according to the invention therefore permits conserving the initial primary or secondary amine functions and this is done advantageously in the absence of any prior protection.

They are therefore able to give rise to all known reactions of primary or secondary amines.

The following examples illustrate the invention without, however, limiting its scope.

EXAMPLE 1

Synthesis of the compound conforming to the formula:

$CH_3-NH-(CH_2CH_2-O)_{11}-H$ 500 cm³ of anhydrous tetrahydrofuran and 8.05 cm³ N-methylethanolamine (0.1 mole) are introduced under argon into a perfectly anhydrous glass reactor. A solution of diphenylmethylpotassium, or 106.15 cm³ of a solution titrated to exactly 0.95 mole/L, is added dropwise under argon until a persistent orange-brown coloring of the medium is obtained. Partial precipitation of the potassium amino-alcoholate occurs.

While the argon inlets and outlets are kept closed, ethylene oxide, 51 cm³ (1 mole at 20° C.), is introduced in the liquid form, and then the reactor is brought to 30° C. The reactor is thus in an overpressure of approximately 0.2 bar and the mixture is kept stirred at 30° C. for 12 hours. At the end of the reaction, the mixture takes on a copper color. It is acidified by a solution of acid methanol containing 2% hydrochloric acid.

Neutralization is reached when the medium is decolored into a clear yellow. The potassium chloride is eliminated by filtration; the tetrahydrofuran (THF) is evaporated under vacuum and the residue is poured into a mixture made up of 800 cm³ water and 800 cm³ ether.

The aqueous phase contains the aminated polymer specifically polyoxyethylated onto the oxygen of the alcohol function, of which 51.5 g are isolated after total evaporation of the water under vacuum.

The ¹H NMR spectrum (nuclear magnetic resonance of the proton) in the deuterated chloroform is characteristic of the polyoxyethylated product with 11 units of oxyethylene with 1 singlet at 2.4 ppm (N—CH₃)(3H); 1 triplet at 2.7 ppm (N—CH₂)(2H); 1 singlet at 3.64 ppm (CH₂CH₂O)n (42H) and 1 singlet at 3.1 ppm (N—H and O—H)(2H).

The absence of polymer produced by condensation of ethylene oxide on the amine function is demonstrated by the absence of a singlet at 2.3 ppm, which would correspond to the presence of a methyl on a tertiary nitrogen. Gel permeation chromatography (GPC) in water provides a chromatogram (previously standardized by a standard polyoxyethylene scale) whose maximum is situated at $M_w$=520, in agreement with the expected mass.

EXAMPLE 2

Synthesis of the compound conforming to the formula:

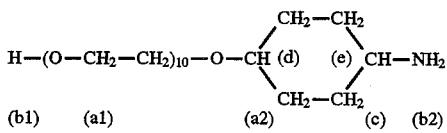

According to the operating mode previously described in Example 1, 11.5 g (0.1 mole) of 4-amino cyclohexanol are dissolved in 500 mL of THF. Then 100 mL (0.1 mole) of 1M diphenylmethylpotassium in THF are added, followed by 51 mL (1 mole) ethylene oxide. After 20 h of reaction at 30° C., the mixture is treated as indicated in Example 1.

By ¹H NMR the following peaks are found:

a multiplet at 3.64 ppm corresponding to 41H designated by a1 and a2 a singlet at 3.10 ppm corresponding to 3H designated by b1 and b2 a quintuplet at 2.7 ppm corresponding to 1H designated by c a multiplet at 2.01 ppm corresponding to 4H designated by d a multiplet at 1.25 ppm corresponding to 4H designated by e.

By GPC in water (chromatogram standardized as previously), a molecular weight (Mw) equal to 550 g/mole is found.

EXAMPLE 3

Synthesis of the compound conforming to the formula:

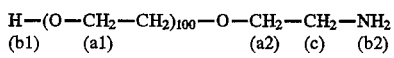

$H-(O-CH_2-CH_2)_{100}-O-CH_2-CH_2-NH_2$
(b1)　　　(a1)　　　　　(a2)　(c)　(b2)

This compound is synthesized according to the operating mode described in Example 1 from 6.11 g of ethanolamine (0.01 mole), 10 moles of 1M diphenylmethylpotassium (0.01 mole) and 51 mL of ethylene oxide (1 mole).

By ¹H NMR, the following peaks are found:

a multiplet at 3.64 ppm corresponding to 402H designated by a1 and a2 a singlet at 3.05 pm corresponding to 3H designated by b1 and b2 a triplet at 2.70 ppm corresponding to 2H designated by c

By GPC (H₂O) is found a molecular weight Mw equal to 4,200 g/mole.

EXAMPLE 4

According to the operating mode described in Example 1, the product conforming to the formula:

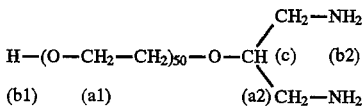

is synthesized from 1.8 g of diamino 2-propanol (0.02 mole), 20 mL of 1M diphenylmethylpotassium (0.02 mole) and 51 mL of ethylene oxide (1 mole).

The following is found by ¹H NMR on the product obtained:

a multiplet at 3.64 ppm corresponding to 201H designated by a1 and a2 a singlet at 3.05 ppm corresponding to 5H designated by b1 and b2 a multiplet at 2.70 ppm corresponding to 4H designated by c

By GPC (H₂O), a molecular weight equal to 2,250 g/mole is found.

EXAMPLE 5

According to the operating mode described in Example 1, the product conforming to the following formula is synthesized:

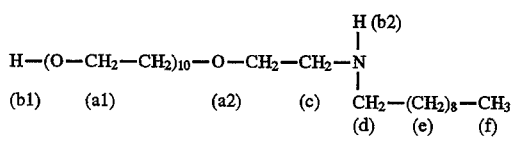

with 10.5 g of N-decylethanolamine (0.05 mole), 100 mL of 1M diphenylmethylpotassium (0.05 mole) and 51 mL ethylene oxide (1 mole).

The following spectrum is found by $^1$H NMR:
- a multiplet at 3.64 ppm corresponding to 42H designated by a1 and a2
- a singlet at 3.10 ppm corresponding to 2H designated by b1 and b2
- a triplet at 2.7 ppm corresponding to 2H designated by c
- a triplet at 2.4 ppm corresponding to 2H designated by d
- a multiplet at 1.35 ppm corresponding to 16H designated by e
- a triplet at 0.95 ppm corresponding to 3H designated by f.

By GPC (H$_2$O), a molecular weight Mw equal to 1,050 g/mole is found.

EXAMPLE 6

Polyoxyalkylation from a compound having sodium alcoholate functions:

One proceeds as indicated in Example 1 with 7.51 g of N-methylethanolamine (0.1 mole), 100 mL of 1M diphenylmethylsodium (0.1 mole) and 51 mL ethylene oxide (1 mole).

After 20 h of reaction, the conversion of ethylene oxide is 55%.

By $^1$H NMR, the following spectrum is found:
- 1 singlet at 2.43 ppm corresponding to a methyl fixed on a secondary nitrogen
- 1 singlet at 2.31 ppm corresponding to a methyl fixed on a tertiary nitrogen.

The amount of tertiary amine is 40% (by moles).

EXAMPLE 7

Polyoxyalkylation from a mixture obtained by conversion of 10% of the OH groups into OK groups:

One operates according to the operating mode described in Example 1, with 6.11 g of ethanolamine (0.1 mole), 10 mL of 1M diphenylmethylpotassium (0.01 mole) and 51 mL ethylene oxide (1 mole).

After 120 h of reaction at 30° C., the conversion of ethylene oxide is only 22%, the amount of secondary amine is 28% (by moles) and the amount of tertiary amine is 19% (by moles).

EXAMPLE 8

Polyoxyalkylation from a mixture obtained by conversion of 50% of the OH groups into OK groups:

One operates again according to the operating mode described in Example 1 with 6.11 g of ethanolamine (0.1 mole), 50 mL of 1M diphenylmethylpotassium (0.05 mole) and 51 mL ethylene oxide (1 mole).

After 20 h of reaction at 30° C., the conversion of ethylene oxide is 95%. The amount of primary amine is 93%, and that of secondary amine is 7% (expressed in moles).

EXAMPLE 9

Polyoxyalkylation from a mixture obtained by conversion of 75% of the OH groups into OK groups:

According to the operating mode described in Example 1, the product corresponding to the following formula is synthesized:

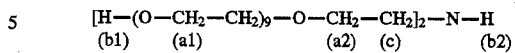

50 mL of 1M diphenylmethylpotassium (0.05 mole) are introduced into 500 cm$^3$ of THF, followed by 5.25 g of diethanolamine (0.05 mole), and then 25 mL of diphenylmethylpotassium solution (0.025 mole). Finally, 51 mL ethylene oxide are added.

One proceeds as in Example 1 with the exception that it is left to react for 20 hours:

The $^1$H NMR spectrum of the product obtained is the following:
- a multiplet at 3.64 ppm corresponding to 76H designated by a1 and a2
- a singlet at 3.15 ppm corresponding to 3H designated by b1 and b2
- a triplet at 2.65 ppm corresponding to 4H designated by c The product then contains approximately 5% by moles of tertiary amine.

The molecular mass obtained by GPC is equal to 900 g/mole.

We claim:

1. Process for the preparation of compounds containing at least one primary or secondary amine function and at least one polyoxyalkylated chain, comprising:

replacing a fraction or all of the OH groups of an amino-alcohol (A) having at least one OH group and at least one primary amine or secondary function, by OM groups, M being an atom selected from the group consisting of sodium, potassium, rubidium and cesium, in order to obtain an amino-alcoholate (B), said amino-alcohol (A) and amino-alcoholate (B) being free of groups reactive with each other or with a function carried by amino-alcohol (A) or amino-alcoholate (B) under the reaction conditions of the process;

reacting said amino-alcoholate (B) with an oxirane, a mixture of oxiranes or a sequence of oxiranes, in an aprotic and anhydrous solvent, under an anhydrous atmosphere and at a temperature between about 0° and 200° C., thereby affixing onto each oxygen atom originating either from an OH group or an OM group, at least one unit conforming to the formula:

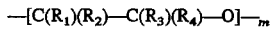

wherein m is a whole number greater than or equal to 1, and in which $R_1$, $R_2$, $R_3$ and $R_4$ are similar or different and are selected from the group consisting of a hydrogen atom, a monovalent radical, saturated or unsaturated, alkyl, cycloalkyl and aryl radicals, said radicals containing substituents unreactive with regard to an amine function and an alcoholate function.

2. Process according to claim 1 wherein the process is for the preparation of compounds containing at least one primary amine function and at least one polyoxylate chain and the amino-alcohol (A) contains at least one OH group and at least one primary amine function.

3. Process according to claim 2 wherein m is a number between 1 and 10,000.

4. Process according to claim 3 wherein m is a number between 1 and 500.

5. Process according to claim 4 wherein m is a number between 1 and 250.

6. Process according to claim 2 wherein M is selected from the group consisting of potassium, rubidium and cesium.

7. Process according to claim 6 wherein M is potassium.

8. Process according to claim 2 wherein the amino-alcohol (A) conforms to the following formula:

$$[(HNRi)jQ](OH)_{(r+q)}$$

in which j is the number of primary amine functions, which are identical or different from one another, j varying from 1 to 10 inclusive;

r is the sum of the number of OH groups carried by all the Ri groups, and q is the number of OH groups carried by Q, r+q being greater than or equal to 1;

Q represents an organic radical comprising 2 to 50 carbon atoms;

each Ri is a hydrogen atom or an organic radical comprising from 1 to 50 carbon atoms;

when the amino-alcohol (A) contains more than one primary amine function, the Ri groups can be similar to or different from one another;

Q and Ri can be heteroatom carders and/or can have various substituents;

Q, N and Ri can form together one or several rings, said ring or rings containing one or more other heteroatoms, and Q and Ri are free of groups reactive with each other or with other groups carried by amino-alcohol (A) or amino-alcoholate (B) under the process reaction conditions.

9. Process according to claim 2 wherein the number of OM groups is greater than 30% of the sum of the number of OM groups and the number of OH groups.

10. Process according to claim 2 wherein the oxirane reactant is selected from the group consisting of ethylene oxide, propylene oxide, butylene oxide, amylene oxide, octylene oxide, styrene oxide, methylstyrene, cyclohexane oxide, their various substituted derivatives and mixtures thereof.

11. Process according to claim 10 wherein the oxirane is selected from the group consisting of ethylene oxide, propylene oxide, styrene oxide and mixtures thereof.

12. Process according to claim 11 wherein the oxirane is ethylene oxide.

13. Process according to claim 2 wherein the aprotic and anhydrous solvent is tetrahydrofuran, diglyme, dimethyl sulfoxide or hexamethyl phosphoramide.

14. Process according to claim 2 wherein the addition of oxirane is effected at a temperature between about 20° and 120° C.

15. Process according to claim 2, wherein the amino-alcohol (A) is ethanolamine, the propanolamines, 4-amino-cyclohexanol, or diamino-2-propanol.

16. Process for the preparation of compounds containing at least one secondary amine function and at least one polyoxyalkylated chain, comprising:

replacing at least 30% of the OH groups of an amino-alcohol (A) having at least one OH group and at least one secondary amine function, by OM groups, M being an atom selected from the group consisting of sodium, potassium, rubidium and cesium, in order to obtain an amino-alcoholate (B), said amino-alcohol (A) and amino-alcoholate (B) being free of groups reactive with each other or with a function carried by amino-alcohol (A) or amino-alcoholate (B) under the reaction conditions of the process;

reacting said amino-alcoholate (B) with an oxirane, a mixture of oxiranes or a sequence of oxiranes, in an aprotic and anhydrous solvent, under an anhydrous atmosphere and at a temperature between about 0° and 200° C., thereby affixing onto each oxygen atom originating either from an OH group or an OM group, at least one unit conforming to the formula:

$$-[C(R_1)(R_2)-C(R_3)(R_4)-O]-_m$$

wherein m is a whole number greater than or equal to 1, and in which $R_1$, $R_2$, $R_3$, and $R_4$ are similar or different and are selected from the group consisting of a hydrogen atom, a monovalent radical, saturated or unsaturated, alkyl, cycloalkyl and aryl radicals said radicals containing substituents unreactive with an amine function and an alcoholate function.

17. Process according to claim 16 wherein m is a number between 1 and 10,000.

18. Process according to claim 17 wherein m is a number between 1 and 500.

19. Process according to claim 18 wherein m is a number between 1 and 250.

20. Process according to claim 16 wherein M is selected from the group consisting of potassium, rubidium and cesium.

21. Process according to claim 20 wherein M is potassium.

22. Process according to claim 16 wherein the amino-alcohol (A) conforms to the following formula:

$$[(HNRi)jQ](OH)_{(r+q)}$$

in which j is the number of secondary amine functions, which are identical or different from one another, j varying from 1 to 10 inclusive, r is the sum of the number of OH groups carried by all the Ri groups, and q is the number of OH groups carried by Q, r+q being greater than or equal to 1, Q represents an organic radical comprising 2 to 50 carbon atoms, each Ri is a hydrogen atom or an organic radical comprising from 1 to 50 carbon atoms, when the amino-alcohol (A) contains more than one secondary amine function, the Ri groups can be similar to or different from one another, Q and Ri can be heteroatom carders and/or can have various substitutents, Q, N and Ri can form together one or several rings, said ring or rings containing one or more other heteroatoms, and Q and Ri are free of groups reactive with each other or with other groups carried by amino alcohol (A) or amino-alcoholate (B) under the process reaction conditions.

23. Process according to claim 16 wherein the oxirane reactant is selected from the group consisting of ethylene oxide, propylene oxide, butylene oxide, amylene oxide, octylene oxide, styrene oxide, methylstyrene, cyclohexane oxide, their various substituted derivatives and mixtures thereof.

24. Process according to claim 23 wherein the oxirane is selected from the group consisting of ethylene oxide, propylene oxide, styrene oxide and mixtures thereof.

25. Process according to claim 24 wherein the oxirane is ethylene oxide.

26. Process according to claim 16 wherein the aprotic and anydrous solvent is tetrahydrofuran, diglyme, dimethyl sulfoxide or hexamethyl phosphoramide.

27. Process according to claim 16 wherein the addition of oxirane is effected at a temperature between about 20° and 120° C.

28. Process according to claim 16 wherein the aminoalcohol (A) is diethanolamine, N-methylethanolamine, or N-decylethanolamine.

29. Process according to claim 16 wherein the reaction is followed by a neutralization or functionalization step for each oxygen atom terminating a polyoxylkylated chain.

* * * * *

UNITED STATES PATENT AND TRADEMARK OFFICE
CERTIFICATE OF CORRECTION

PATENT NO. : 5,629,452
DATED : May 13, 1997
INVENTOR(S) : Mosquet et al.

It is certified that error appears in the above-identified patent and that said Letters Patent is hereby corrected as shown below:

Column 11, claim 8,
Line 24, delete "carders" and insert -- carriers --.

Column 12, claim 22,
Line 49, delete "carders" and insert -- carriers --.

Column 11, claim 10,
Line 40, delete "methylstyrene" and insert -- methylstyrene oxide --.

Signed and Sealed this

Sixth Day of November, 2001

*Attest:*

*Attesting Officer*

NICHOLAS P. GODICI
*Acting Director of the United States Patent and Trademark Office*